(12) United States Patent
Cui et al.

(10) Patent No.: US 12,296,568 B2
(45) Date of Patent: May 13, 2025

(54) SYSTEMS AND METHODS FOR HEAT CONDUCTING AND BIOFLUID TRANSPORTING TEXTILE

(71) Applicant: The Board of Trustees of the Leland Stanford Junior University, Stanford, CA (US)

(72) Inventors: Yi Cui, Stanford, CA (US); Shanhui Fan, Stanford, CA (US); Yucan Peng, Stanford, CA (US); Wei Li, Stanford, CA (US); Bofei Liu, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 405 days.

(21) Appl. No.: 17/357,798

(22) Filed: Jun. 24, 2021

(65) Prior Publication Data

US 2021/0402734 A1 Dec. 30, 2021

Related U.S. Application Data

(60) Provisional application No. 63/043,982, filed on Jun. 25, 2020.

(51) Int. Cl.
  *B32B 3/30* (2006.01)
  *B32B 5/26* (2006.01)
  (Continued)

(52) U.S. Cl.
  CPC ............... *B32B 3/30* (2013.01); *B32B 5/262* (2021.05); *B32B 15/14* (2013.01); *B32B 15/20* (2013.01);
  (Continued)

(58) Field of Classification Search
  CPC ........... B32B 3/30; B32B 5/262; B32B 15/14; B32B 15/20; B32B 27/12; B32B 27/32;
  (Continued)

(56) References Cited

U.S. PATENT DOCUMENTS

2003/0220048 A1* 11/2003 Toro ................... A61F 13/141
  450/57
2014/0288515 A1* 9/2014 Pan .................... A61B 10/0064
  604/290
(Continued)

FOREIGN PATENT DOCUMENTS

JP 2005015969 A * 1/2005

OTHER PUBLICATIONS

SewPort "What is Coolmax fabric?" https://sewport.com/fabrics-directory/coolmax-fabric Retrieved Jun. 9, 2024 (Year: 2024).*
(Continued)

*Primary Examiner* — Alicia J Weydemeyer
*Assistant Examiner* — Laura B Figg
(74) *Attorney, Agent, or Firm* — Foley & Lardner LLP

(57) ABSTRACT

Example implementations include a textile apparatus for transporting perspiration and heat, the textile apparatus including a substantially planar and heat-conducting substrate including at least one recess, and a textile film including one or more fibers disposed in contact with at least one substantially planar surface of the substrate and at least one surface of the recess. Example implementations also include a method of manufacturing a textile apparatus for transporting perspiration and heat, the method including forming a nanofiber solution, extruding one or more nanofibers from the nanofiber solution, forming one or more recesses in a substantially planar surface of a substrate, and
(Continued)

integrating one or more of the nanofibers with the substantially planar surface of the substrate and at least one surface of the recesses.

11 Claims, 12 Drawing Sheets

(51) Int. Cl.
  *B32B 15/14* (2006.01)
  *B32B 15/20* (2006.01)
  *B32B 27/12* (2006.01)
  *B32B 27/32* (2006.01)
  *G01N 33/36* (2006.01)

(52) U.S. Cl.
  CPC .............. *B32B 27/12* (2013.01); *B32B 27/32* (2013.01); *G01N 33/367* (2013.01); *B32B 2250/02* (2013.01); *B32B 2262/0253* (2013.01); *B32B 2307/302* (2013.01); *B32B 2307/726* (2013.01)

(58) Field of Classification Search
  CPC ........ B32B 2250/02; B32B 2262/0253; B32B 2307/302; B32B 2307/726; G01N 33/367
  See application file for complete search history.

(56) References Cited

U.S. PATENT DOCUMENTS

| | | | | |
|---|---|---|---|---|
| 2016/0299543 | A1* | 10/2016 | Brooks | A61F 7/007 |
| 2016/0374411 | A1* | 12/2016 | Brooks | A61F 7/007 165/104.21 |
| 2019/0008217 | A1* | 1/2019 | Cui | D06M 15/3562 |

OTHER PUBLICATIONS

Scranton "Green Chemistry, Industrial Chemistry Module" https://www.scranton.edu/faculty/cannm/green-chemistry/english/industrialchemistrymodule.shtml Retrieved Jun. 9, 2024 (Year: 2024).*
JP-2005015969-A English translation from Search (Year: 2005).*

* cited by examiner

SYSTEMS AND METHODS FOR HEAT CONDUCTING AND BIOFLUID TRANSPORTING TEXTILE

CROSS-REFERENCE TO RELATED PATENT APPLICATIONS

This application claims priority to U.S. Provisional Patent Application Ser. No. 63/043,982, entitled "INTEGRATED COOLING TEXTILE OF HEAT CONDUCTION AND SWEAT TRANSPORTATION FOR PERSONAL PERSPIRATION MANAGEMENT," filed Jun. 25, 2020, the contents of all such applications being hereby incorporated by reference in its entirety and for all purposes as if completely and fully set forth herein.

TECHNICAL FIELD

The present implementations relate generally to textiles, and more particularly to a heat conducting and biofluid transporting textile.

BACKGROUND

Maintaining a particular body temperature and preventing overheating is critical to health and safety for humans and many animals. Physiological and psychological problems resulting from body overheating can be threatening for human health, and also influence labor productivity and society economy negatively. In general, the human body dissipates heat via heat transfer pathways including conduction and evaporation. For the delicate human body system with a narrow range for healthy body temperature, evaporation plays an indispensable role in human body thermoregulation. Healthy human core temperature at rest can range from 36-38° C., and can range up to 41° C. during heavy exercise. About 20 percent of heat dissipation of the dry human body relies on the water vapor loss via insensible perspiration. As heat load on the human body increases, sweat evaporation can account for more and more heat loss and can become the major route for human body heat dissipation in intense scenarios such as heavy exercise and hot/humid environments. In these scenarios excess heat cannot be dissipated efficiently by heat transfer pathways other than conduction and evaporation by perspiration. However, conventional textiles cannot effectively and efficiently achieve sufficient heat transfer by personal perspiration or evaporation management.

SUMMARY

Present implementations are directed to a heat conducting and biofluid transporting textile capable of transferring heat and biofluid from a biofluid-emitting biological surface. The example textile in accordance with present implementations can advantageously direct biofluid through the textile from a surface in contact with the biological surface to an opposite surface of the textile in contact with an ambient environment. Thus, the textile can be at least part of an article of clothing worn by a human and in at least partial contact with the skin of the wearing human. The biofluid can be sweat, perspiration, and the like, and can include artificial perspiration and other types of biofluid dischargeable from the biological surface or present on the biological surface.

Present implementations can advantageously transfer increased heat away from a biological surface with a heat-conductive substrate having relatively lower liquid absorptive properties. The heat-conductive substrate can be contactable with a biological surface to absorb heat therefrom and to transmit heat therethrough. Present implementations can also include a biofluid-absorptive textile film integrated with the substrate. The textile film can be located on the second surface of the substrate and can be contactable with the ambient environment at least when the substrate is in contact with the biological surface. In some implementations, the substrate includes channels, opening, or the like therethrough, allowing the textile film to contact the biological surface at one or more points. The textile film can then absorb biofluid at the biological surface and wick it to the opposite surface facing the ambient environment. Heat transferred to the substrate can advantageously evaporate biofluid located on or within the textile film, resulting in a transfer of heat from the biological surface through the ambient environment by an enhanced biofluid evaporation process that reduces the amount of biofluid needed to transfer body heat from the biological surface to the ambient environment, and thus advantageously cool the wearer of the example textile in accordance with present implementations. Thus, a technological solution for a heat conducting and biofluid transporting textile is provided.

Example implementations include a textile apparatus for transporting perspiration and heat, the textile apparatus including a substantially planar and heat-conducting substrate including at least one recess, and a textile film including one or more fibers disposed in contact with at least one substantially planar surface of the substrate and at least one surface of the recess.

Example implementations also include a textile apparatus where the substrate includes a copper sheet.

Example implementations also include a textile apparatus where the substrate includes a nanoporous polyethylene sheet.

Example implementations also include a textile apparatus where the substrate includes a textile including one or more woven polyethylene fibers.

Example implementations also include a textile apparatus where the recess includes one or more cavities through the substrate.

Example implementations also include a textile apparatus where one or more of the fibers of the textile film are disposed at least partially within one or more of the cavities.

Example implementations also include a method of manufacturing a textile apparatus for transporting perspiration and heat, the method including forming a nanofiber solution, extruding one or more nanofibers from the nanofiber solution, forming one or more recesses in a substantially planar surface of a substrate, and integrating one or more of the nanofibers with the substantially planar surface of the substrate and at least one surface of the recesses.

Example implementations also include a method further including coating one or more woven polyethylene fibers with polydopamine, where the substrate includes the woven polyethylene fibers.

Example implementations also include a method further including coating the polydopamine coating of the polyethylene fibers with a plating seed layer.

Example implementations also include a method where the coating the polyethylene fibers with the plating seed layer includes immersing the polyethylene fibers in a solution including silver nitrate.

Example implementations also include a method further including coating the plating seed layer coating of the polyethylene fibers with a plating layer.

Example implementations also include a method where the coating the plating seed layer coating of the polyethylene fibers with the plating layer includes immersing the polyethylene fibers in a solution including $Ag(NH_3)_2^+$.

Example implementations also include a method further including forming one or more biofluid transport channels in the substrate.

Example implementations also include a method where the forming the biofluid transport channels in the substrate includes cutting the substrate with an ultraviolet laser.

Example implementations also include a method where the substrate includes a copper sheet.

Example implementations also include a method where the substrate includes a nanoporous polyethylene sheet.

Example implementations also include a method where the integrating one or more of the nanofibers with the substantially planar surface of the substrate and at least one surface of the recesses includes pressing the nanofibers onto the substantially planar surface of the substrate and at least one surface of the recesses by a hydraulic press.

Example implementations also include an apparatus for simulating artificial perspiration to test a textile apparatus for transporting perspiration and heat, the apparatus including a liquid reservoir including a flow inlet, a flow outlet, and one or more simulated perspiration outlets, a perforated heater layer disposed on the liquid reservoir proximate to the simulated perspiration outlets, a wicking layer disposed on the perforated heater layer, and a hydrophobic layer disposed on the wicking layer and including one or more openings.

Example implementations also include an apparatus where the openings of the hydrophobic layers are configured to transmit liquid from the liquid reservoir therethrough.

Example implementations also include an apparatus where the hydrophobic layers are configured to transmit liquid from the liquid reservoir by a capillary force.

BRIEF DESCRIPTION OF THE DRAWINGS

These and other aspects and features of the present implementations will become apparent to those ordinarily skilled in the art upon review of the following description of specific implementations in conjunction with the accompanying figures, wherein.

DETAILED DESCRIPTION

Figure 1A:
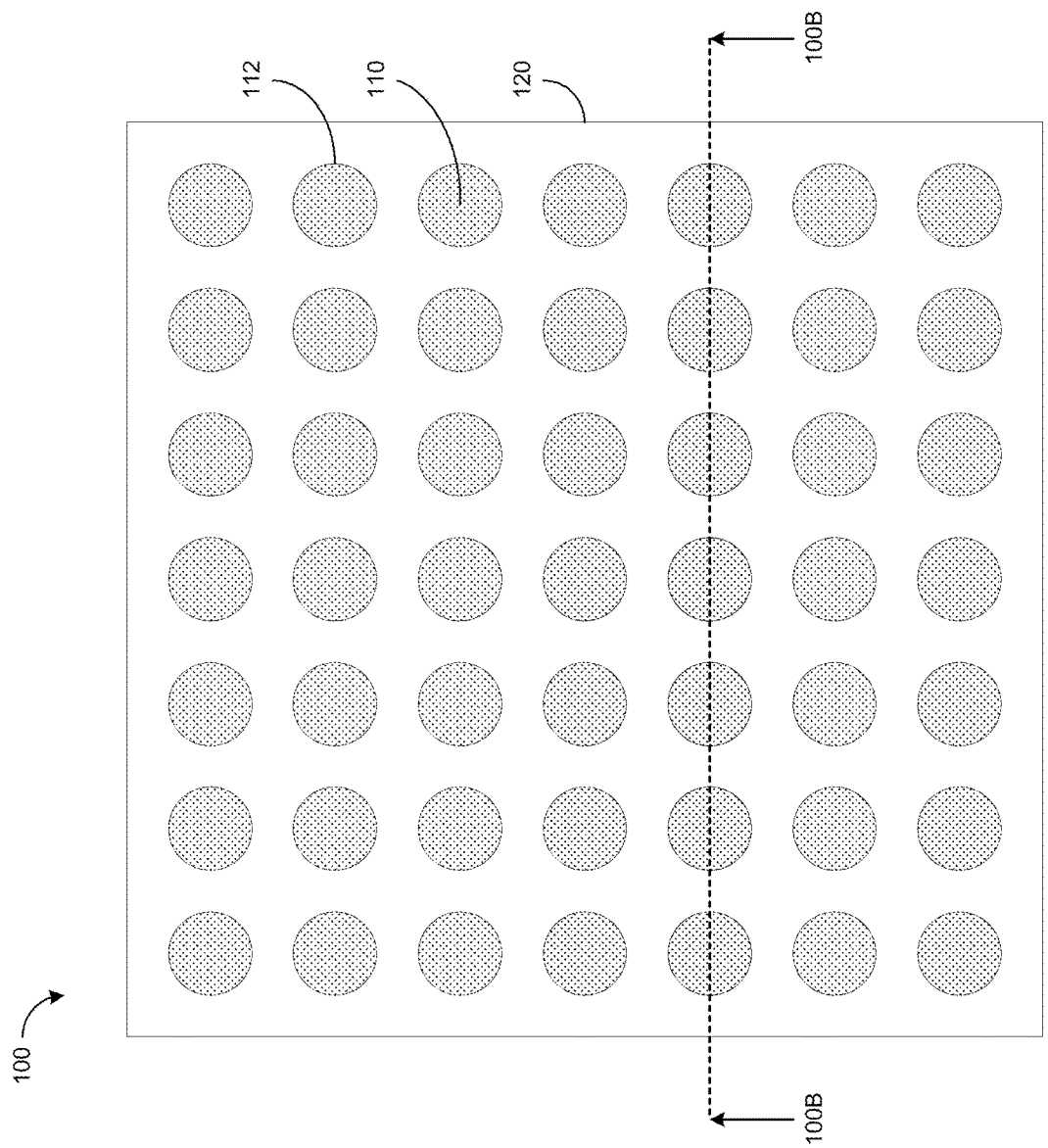
FIG. 1A illustrates an example plan view of a first example heat conducting and biofluid transporting textile, in accordance with present implementations.

The present implementations will now be described in detail with reference to the drawings, which are provided as illustrative examples of the implementations so as to enable those skilled in the art to practice the implementations and alternatives apparent to those skilled in the art. Notably, the figures and examples below are not meant to limit the scope of the present implementations to a single implementation, but other implementations are possible by way of interchange of some or all of the described or illustrated elements. Moreover, where certain elements of the present implementations can be partially or fully implemented using known components, only those portions of such known components that are necessary for an understanding of the present implementations will be described, and detailed descriptions of other portions of such known components will be omitted so as not to obscure the present implementations. Implementations described as being implemented in software should not be limited thereto, but can include implementations implemented in hardware, or combinations of software and hardware, and vice-versa, as will be apparent to those skilled in the art, unless otherwise specified herein. In the present specification, an implementation showing a singular component should not be considered limiting; rather, the present disclosure is intended to encompass other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present implementations encompass present and future known equivalents to the known components referred to herein by way of illustration.

Conventional textiles cannot rapidly evaporate sweat by taking advantage of human body, due to the low thermal conductance of textiles. Further, where sweat evaporation occurs on the textiles, only a textile surface rather than skin underneath the textile can be efficiently cooled. The sweat absorbed by the conventional textiles is not useful for cooling down the human body. Thus, the cooling power associated with conventional textile evaporation cannot be efficiently delivered to the human body. Inefficient cooling can lead to further perspiration, and meanwhile the slow sweat evaporation can result in the accumulation of sweat in the textile. This process can rapidly compound to undermine the temperature buffer effect of the textiles due to the absorption limit of the fabric. The human body can, as a result, maintain an unpleasant and health-reducing biofluid trapped on the biological surface and the conventional textile. Further perspiration of biofluid in response to the previously and ineffectively perspired biofluid can result in potential risk of dehydration, electrolyte disorder, physical and mental deterioration or even death. Conventional textiles do not perform ideally in profuse perspiration situations. Therefore, a textile for personal perspiration management which is capable of fast wicking, rapid evaporating sweat, cooling down skin efficiently and reducing body water loss is needful and significant.

Present implementations include a wearable and washable textile for personal perspiration management, with heat conduction and sweat transportation for personal perspiration management. Example textiles in accordance with present implementations include heat conductive components integrated into the textile and advantageously divide the responsibilities of heat conduction and water transport across two functional components integrated within the textile. Thus, a heat conductive matrix and biofluid transportation channels can be integrated together to perform different functions with a synergistic effect maximizing sweat transport, rapid evaporation, evaporative cooling and reducing human body dehydration. Example textiles in accordance with present implementations have multiple advantages based on the heat conductive matrix and the biofluid transportation channels. Absorbed biofluid (e.g., sweat) in the biofluid transportation channels of the example textile can be effective for cooling down the human body by rapid evaporation removing significant amounts of heat from the skin through direct contact with skin. This rapid evaporation and efficient cooling effect can prevent the example textile from flooding to a much greater extent and avoid excessive perspiration. Thus, example textiles in accordance with present implementations can help the human body achieve an enhanced cooling effect while consuming greatly reduced sweat by a combination of efficient and concurrent heat conduction and biofluid transportation away from the biological surface (e.g., skin).

water transport channels shoulder the responsibility of pulling water up from skin and spreading it on the top surface for evaporation. On the other hand, the heat conductive matrix transfers heat from skin to the top evaporation layer very efficiently. Water tends to be absorbed by the water transport channels rather than the heat conductive matrix since the heat conductive matrix is designed to not wick water on purpose. Thus, the area of "wet skin" can be decreased, and meanwhile the thermal conduction through heat conductive matrix can be maintained the furthest avoiding the thermal resistance of water. Accordingly, combined with large evaporation area and efficient heat conduction from skin, sweat wicked onto the top surface can be evaporated quickly into air, taking away a huge amount of heat from the skin. Notably, due to the great heat conduction capability of the heat conductive matrix, the evaporative cooling effect can in return decrease skin temperature, which will consequently reduce human body dehydration. the key factor to achieve effective cooling effect is the integrated functional design of heat conduction and sweat transportation rather than simply reducing textile's area mass density/thickness.

FIG. 1A illustrates an example plan view of a first example heat conducting and biofluid transporting textile, in accordance with present implementations. As illustrated by way of example in FIG. 1A, an example plan view 100A includes a first example heat conducting and biofluid transporting textile with a textile film 110 including biofluid transportation channels 112 and a substrate sheet 120.

The textile film 110 includes one or more fibers formed into a textile sheet and integrable with the substrate 120. The textile film 110 can include a collection of fibers collected into a substantially planar sheet structure. It is to be understood that the fibers of the textile film can be collected and located proximate to each other, and are not limited to a woven configuration. In some implementations, the fibers can be nanofibers with water absorbing properties. As one example, the nanofibers can include nylon 6. Nylon 6 has water-wicking properties advantageous for biofluid transportation. It is to be understood that the fibers or nanofibers of the textile film can include material other than nylon 6, and are not limited to nylon 6. The nanofibers can have a diameter less than 5 μm, and can be arranged in a substantially integrated structure in response to pressing the nanofibers into integrated contact, permanent contact, adhesion, or the like, with each other. The textile film 110 can be disposed integrably with the substrate sheet 120 in contact with one or more external planar surfaces and internal cavity, opening, or like surfaces within the substrate sheet 120.

The biofluid transportation channels 112 include at least portions of the textile film 110 disposed at least partially within at least one internal cavity, opening, or like surfaces within the substrate sheet 120. The biofluid transportation channels 112 can include portions of nanofibers pressed at least partially into at least one internal cavity, opening, or like surfaces within the substrate sheet 120. The biofluid transportation channels 112 can be disposed through an entire cross-sectional dimension of the substrate sheet 120, and can be directly contactable with a biological surface concurrently with the substrate sheet 120. Thus, the biofluid transportation channels 112 of the textile film 110 can have a surface facing a biological surface and be substantially flush with a corresponding surface of the substrate sheet 120. This flush surface can then absorb biofluid through the biofluid transportation channels 112 into the textile film 110, and can concurrently absorb heat (e.g., body heat) generated by the biological surface into the substrate sheet 120 to heat and efficiently evaporate biofluid in the biofluid transportation channels 112 and the textile film 110.

The substrate sheet 120 includes a substantially planar structure with heat conduction properties, and includes one or more grid of holes, recesses, cavities, openings, or the like, in, through, or the like, the substrate sheet 120. The substrate sheet 120 can include a metallic structure, sheet, film, or the like. As one example, the substrate sheet 120 can include copper (Cu). Copper has advantageous thermal conductivity (~400 $W \cdot m^{-1} \cdot K^{-1}$) and can thus conduct body heat much more efficiently and effectively than conventional textiles. It is to be understood that the substrate sheet 120 can include material other than copper, and are not limited to copper. As one example, the substrate sheet 120 can include a nanoporous polytheylene (nanoPE) sheet, material, or the like. The nanoPE can further be coated with a heat conductive material in accordance with heat conductive materials discussed above with respect to the substrate sheet 120.

Figure 1B:
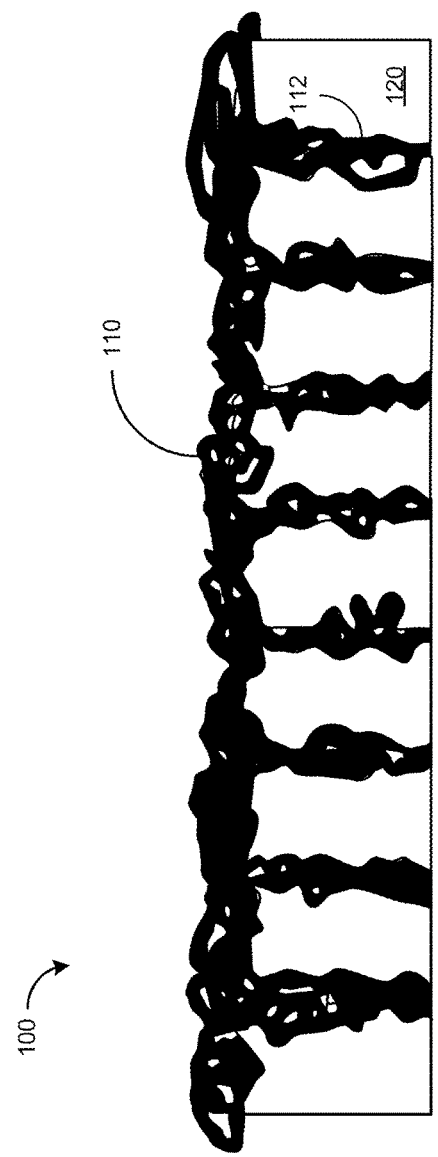
FIG. 1B illustrates an example cross-sectional view of a first example heat conducting and biofluid transporting textile further to the example plan view of FIG. 1A.

FIG. 1B illustrates an example cross-sectional view of a first example heat conducting and biofluid transporting textile further to the example plan view of FIG. 1A. As illustrated by way of example in FIG. 1B, an example cross-sectional view 100B includes the first example heat conducting and biofluid transporting textile with the textile film 110 and the substrate sheet 120.

In the cross-sectional view 100B, the textile film 110 is integrated in contact with an upper planar external surface and multiple internal surfaces of the substrate sheet 120. The textile film 110 can be disposed within the holes, recesses, cavities, openings, or the like, in, through, or the like, the substrate sheet 120. As illustrated in FIG. 1B, the textile film 110 is disposed through the substrate sheet 120 to form the biofluid transportation channels 112. The biofluid transportation channels 112 can be substantially flush with a lower planar external surface of the substrate sheet 120, and can allow concurrent contact by the biofluid transportation channels 112 and the substrate sheet 120 with a biological surface as discussed above. The lower surface of the substrate 120 including the biofluid transportation channels 112 can be placed in direct contact or contactable with the biological substrate, while the upper surface of the substrate 120 can be placed toward the ambient environment with the textile film 110 in direct contact or contactable with the ambient environment. The first example heat conducting and biofluid transporting textile can be an article of clothing, including but not limited to, a shirt, shorts, pants, tank top, sleeve, headband, or the like. An article of clothing including the first example heat conducting and biofluid transporting textile can also be tailored, fitted, or the like, to maximize contact with the biological surface. As one example, the article of clothing can be constructed as a tailored fitting, slim fitting, compression fitting, or the like. The example textile can thus advantageously demonstrate a better cooling effect and cause less water loss under a wide range of exercise intensities.

Figure 2:
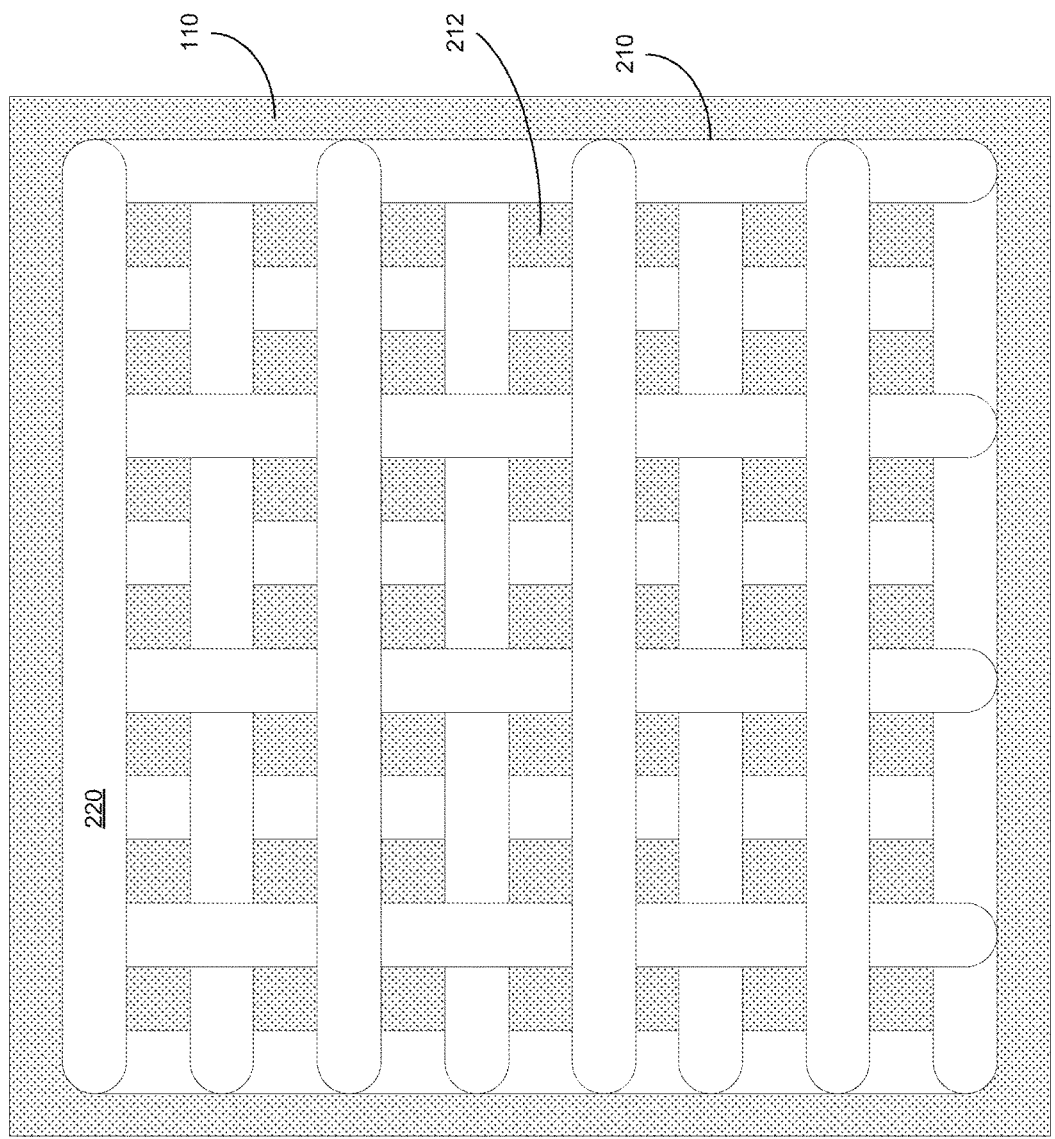
FIG. 2 illustrates an example plan view of a second example heat conducting and biofluid transporting textile, in accordance with present implementations.

FIG. 2 illustrates an example plan view of a second example heat conducting and biofluid transporting textile, in accordance with present implementations. As illustrated by way of example in FIG. 2, an example plan view 200 includes second example heat conducting and biofluid transporting textile with the textile film 110 including biofluid transportation channels 212 and a woven substrate 210 including one or more textile fibers 220.

The woven substrate 210 includes a substantially planar structure with heat conduction properties, and includes one or more fibers arranged to include one or more holes, recesses, cavities, openings, or the like, in, through, or the like, the woven substrate 210. The woven substrate 210 can include a woven fabric structure having a loose weave to produce the holes, recesses, cavities, openings, or the like, in, through, or the like, the woven substrate 210. The woven substrate 210 can include one or more textile fibers 220. The textile fibers 220 can include one or more nonconductive fibers coated with at least one conductive material. As one example, the nonconductive fibers can include polyester (PET) arranged in a loose woven matrix having the biofluid transportation channels 212 of the textile film 110 disposed therebetween. The biofluid transportation channels 212 can have a structure, composition, and the like, corresponding to the structure, composition, and the like of the biofluid transportation channels 112. As another example, the conductive material can include silver (Ag). Silver has advantageous material properties and can resist deterioration, separation, and the like, in response to washing. As one example, a silver-coated polyester woven substrate 210 can maintain 99.5% of its original mass after 50 hours of washing. It is to be understood that the woven substrate 210 can include material other than silver, and is not limited to silver.

Figure 3A:
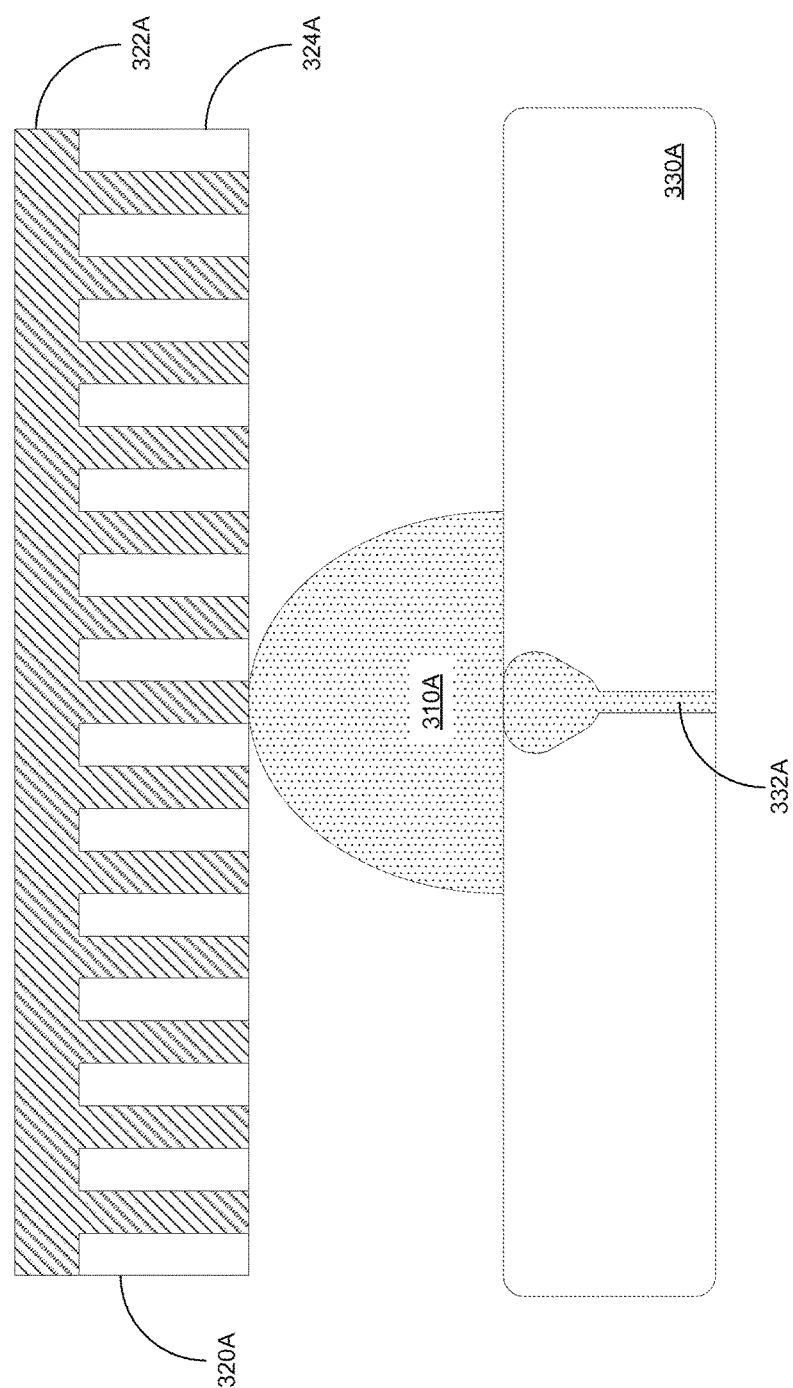
FIG. 3A illustrates an example first state of an example heat conducting and biofluid transporting textile relative to a biological surface, in accordance with present implementations.

FIG. 3A illustrates an example first state of an example heat conducting and biofluid transporting textile relative to a biological surface, in accordance with present implementations. As illustrated by way of example in FIG. 3A, an example first state 300A includes a textile apparatus 320A in a first position with respect to a biological object 330A in a first state. The textile apparatus 320A can include a textile film 322A in a first state and a textile film 322A in a first state. The biological object 330A can include a perspiration duct 332A in a first state and a perspiration effluent 310A in a first state.

The textile apparatus 320A in the first position is disposed proximate to the biological object 330A and the perspiration effluent 310A, and includes the textile film 322A and the substrate 324A respectively facing away from and toward a biological surface of the biological object 330A. The first position of the textile apparatus 320A can be a position out of direct contact with one or more of the perspiration effluent 310A and the biological object 330A. It is to be understood that the textile apparatus 320A can be variously in contact with and out of contact with one or more of the perspiration effluent 310 and the biological object 330 during any of the states 3A-D in accordance with movement and shifting of fabric worn during human activity. The textile film 322A in the first state includes a minimal, reduced, or no amount of liquid, including the perspiration effluent 310B. The textile film 322A can be at a lower temperature than the biological object 330A, and can have a temperature corresponding to an ambient environment surrounding the textile apparatus 320A. The textile film 322A can be contactable with one or more of the perspiration effluent 310A at a lower planar surface of the textile apparatus 320A. The substrate 324A in the first state includes no amount of liquid, including perspiration effluent. The substrate 324A can be at a lower temperature than the biological object 330A, and can have a temperature corresponding to an ambient environment surrounding the textile apparatus 320A. The substrate 324A can be contactable with one or more of the perspiration effluent 310A at a lower planar surface of the textile apparatus 320A.

The biological object 330A in the first state can be in a state of emitting the perspiration effluent 310A by the perspiration duct 332A, and emitting heat. As one example, the biological object 310A can be human skin perspiring during normal activity or exercise activity. The perspiration duct 332A in the first state can produce and emit the perspiration effluent 310A, and can be a human sweat gland. The perspiration effluent 310A in the first state can be emitted from the perspiration duct 332A and deposited on the biological surface of the biological object 330A. The perspiration effluent 310A can include human sweat emitted by human skin onto the surface of the skin.

Figure 3B:
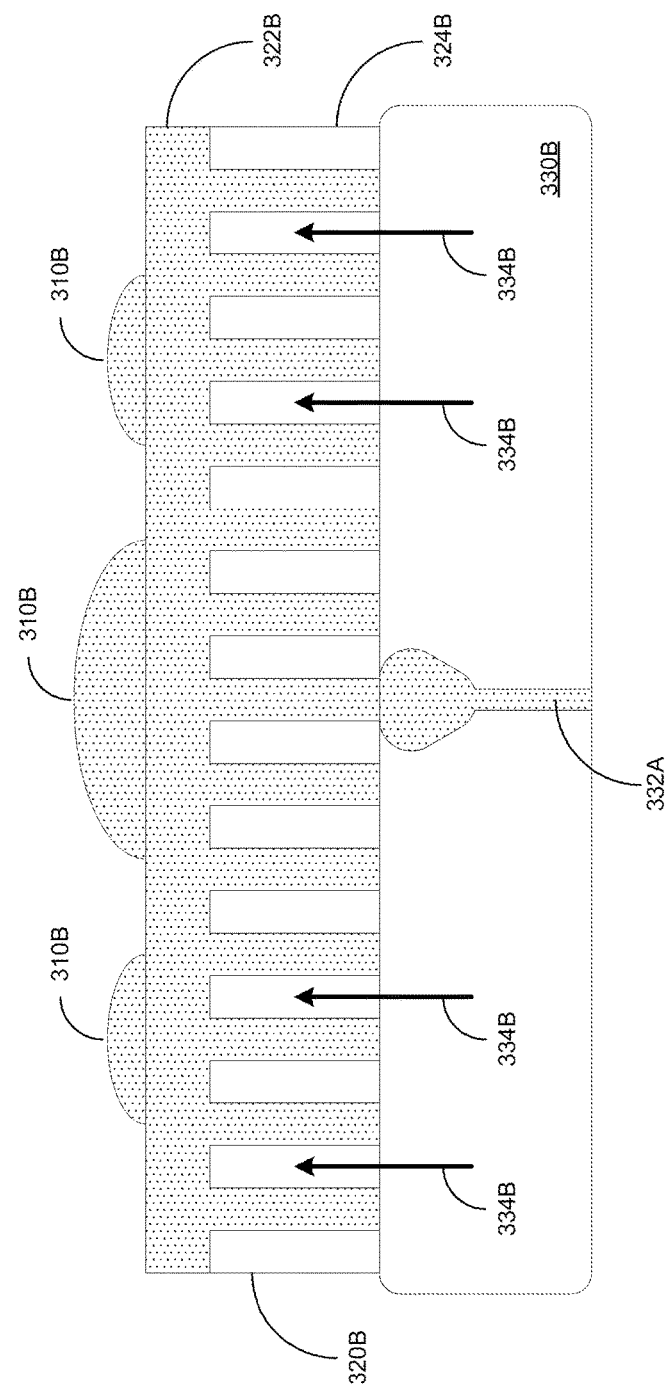
FIG. 3B illustrates an example second state of an example heat conducting and biofluid transporting textile relative to a biological surface, further to the example first state of FIG. 3A.

FIG. 3B illustrates an example second state of an example heat conducting and biofluid transporting textile relative to a biological surface, further to the example first state of FIG. 3A. As illustrated by way of example in FIG. 3B, an example second state 300B includes a textile apparatus 320B in a second position with respect to a biological object 330B in a second state. The textile apparatus 320B can include a textile film 322B in a second state, a substrate 324B in a second state, and a perspiration effluent 310B in a second state. The biological object 330B can include the perspiration duct 332A and can conduct substrate heat 334B to the textile apparatus 320B.

The textile apparatus 320B in the second position is disposed substantially in contact with the biological object 330B and the perspiration effluent 310B, and includes the textile film 322B and the substrate 324B respectively facing away from and substantially in contact a biological surface of the biological object 330B. The second position of the textile apparatus 320B can be a position in direct contact with one or more of the perspiration effluent 310B and the biological object 330B. In response to direct contact with the perspiration effluent 310B, the textile apparatus 320B can absorb the perspiration effluent 310B from the biological surface of the biological object 330B and can transport the perspiration effluent 310B therethrough to the upper surface of the textile apparatus 320B in contact with the ambient environment. The textile film 322B in the second state includes a maximal, increased, or substantial amount of liquid, including the perspiration effluent 310B. The textile film 322B can be at a lower temperature than the biological object 330B, and can have a temperature higher than an ambient environment surrounding the textile apparatus 320B increasing in response to receiving substrate heat 334B received from the biological object 330B. The textile film 322B can be in contact with one or more of the perspiration effluent 310B at least one of a lower planar surface, an upper planar surface of the textile apparatus 320B, and by internal absorption of the perspiration effluent 310B by the textile film 322B. The substrate 324B in the second state continues to include no amount of liquid, including perspiration effluent, and begins to absorb the substrate heat 334B from the biological object 330B and transfer the substrate heat 334B to the textile film 322B and the perspiration effluent 310B. The substrate 324B can be at a lower temperature than the biological object 330B, and can have a temperature higher than an ambient environment surrounding the textile apparatus 320A increasing in response to receiving substrate heat 334B received from the biological object 330B. The substrate 324B can be in contact with the perspiration effluent 310B at one or more of a lower planar surface of the textile apparatus 320B, an upper planar surface of the textile apparatus 320B, and by internal absorption of the perspiration effluent 310B by the textile film 322B.

The biological object 330B in the second state can be in a state of emitting the perspiration effluent 310B by the perspiration duct 332A, and emitting heat. As one example, the biological object 310B can be human skin perspiring during normal activity or exercise activity, and transferring the substrate heat 334B to the substrate 324B by substantially direct contact therewith. The perspiration effluent 310B in the second state can be emitted from the perspiration duct 332A and absorbed at least partially from the biological surface of the biological object 330B to the textile film 322B. Thus, the substrate 324B can efficiently capture more heat from the biological object 330B and heat the perspiration effluent 310B more rapidly through greater surface area contact therewith. As a result, more heat can be transferred from the biological object 330B and the body temperature of a person can be significantly and efficiently reduced by adding to the efficiency of the human perspiration response.

Figure 3C:
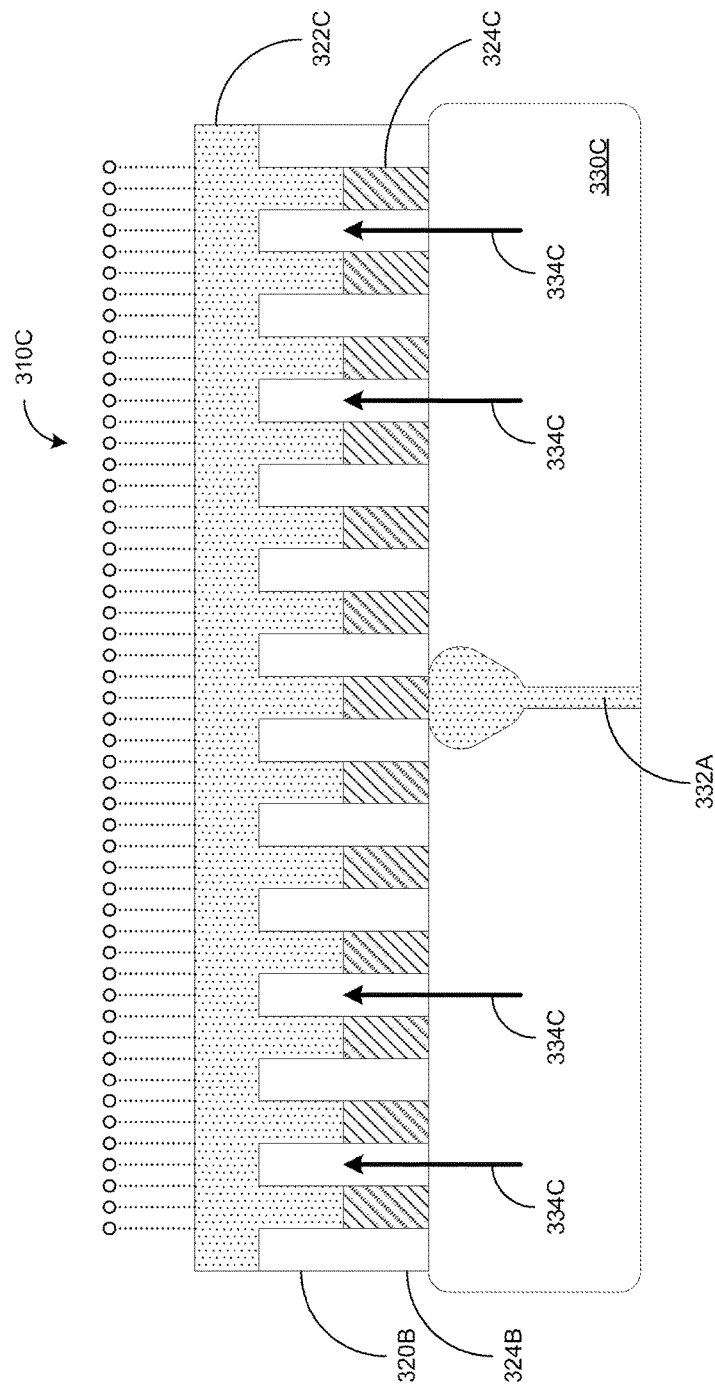
FIG. 3C illustrates an example third state of an example heat conducting and biofluid transporting textile relative to a biological surface, further to the example second state of FIG. 3B.

FIG. 3C illustrates an example third state of an example heat conducting and biofluid transporting textile relative to a biological surface, further to the example second state of FIG. 3B. As illustrated by way of example in FIG. 3C, an example third state 300C includes a textile apparatus 320C in the second position with respect to the biological object 330B. The textile apparatus 320C can include a textile film 322C in a third state and including a drying portion 324C, the substrate 324B in the second state, and a perspiration effluent 310C in a third state. The biological object 330C can include the perspiration duct 332A and can conduct the substrate heat 334B to the textile apparatus 320C.

In response to transfer of the substrate heat 334C to the perspiration effluent 310C, the textile apparatus 320B can begin to evaporate the perspiration effluent 310C from the textile film 322C. The textile film 322C in the third state includes an increased, or substantial amount of liquid, including the perspiration effluent 310C. The textile film 322C can be at a lower temperature than the biological object 330C or a temperature corresponding to the biological object 330C, and can have a temperature higher than an ambient environment surrounding the textile apparatus 320B increasing or maximized in response to receiving substrate heat 334C received from the biological object 330C. The textile film 322C can be in contact with one or more of the perspiration effluent 310C at least one of a lower planar surface, an upper planar surface of the textile apparatus 320B, and by internal evaporation of the perspiration effluent 310C by the textile film 322C. The substrate 324B continues to absorb the substrate heat 334C from the biological object 330C and transfer the substrate heat 334C to the textile film 322C and the perspiration effluent 310C. The substrate 324B can be at a lower temperature than the biological object 330C or a temperature corresponding to the biological object 330C, and can have a temperature higher than an ambient environment surrounding the textile apparatus 320B increasing or maximized in response to receiving substrate heat 334C received from the biological object 330C. The substrate 324B can be in contact with the perspiration effluent 310C at one or more of a lower planar surface of the textile apparatus 320B, an upper planar surface of the textile apparatus 320B, and by internal absorption of the perspiration effluent 310B by the textile film 322B. The drying portion 324C of the textile film 322C can release the perspiration effluent 310C to the ambient environment in response to receiving an amount of substrate heat 334C sufficient to evaporate the perspiration effluent 310C.

The biological object 330C in the third state can be in a state of continuing to emit the perspiration effluent 310C by the perspiration duct 332A, and continuing to further emit heat. As one example, the biological object 310C can be human skin perspiring during normal activity or exercise activity, and transferring the substrate heat 334C to the substrate 324B by substantially direct contact therewith. The perspiration effluent 310C in the third state can be at least partially evaporated from the textile film 322B in response to heating by the substrate heat 334C received from the substrate 324B. Thus, the substrate 324B can efficiently heat the perspiration effluent 310B to evaporation more rapidly through greater surface area contact therewith. As a result, more heat can be transferred from the biological object 330C and the body temperature of a person can be significantly and efficiently reduced by adding to the efficiency of the human perspiration response, including an evaporation response.

Figure 3D:
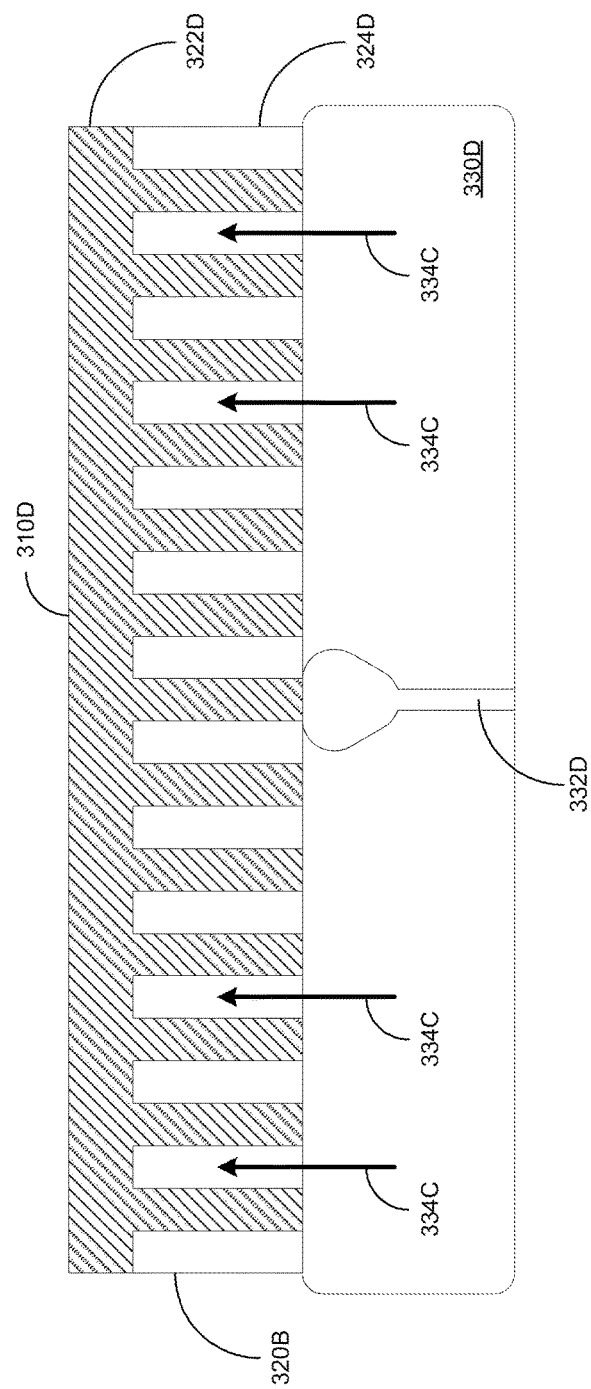
FIG. 3D illustrates an example fourth state of an example heat conducting and biofluid transporting textile relative to a biological surface, further to the example third state of FIG. 3C.

FIG. 3D illustrates an example fourth state of an example heat conducting and biofluid transporting textile relative to a biological surface, further to the example third state of FIG. 3C. As illustrated by way of example in FIG. 3D, an example fourth state 300D includes a textile apparatus 320D in the second position with respect to the biological object 330B. The textile apparatus 320D can include a textile film 322D in a fourth state, the substrate 324B in the second state, and a perspiration effluent 310D in a fourth state. The biological object 330B can include the perspiration duct 332D in a second state and can conduct the substrate heat 334B to the textile apparatus 320D.

In response to further transfer of the substrate heat 334C to the perspiration effluent 310C, the textile apparatus 320B can evaporate substantially all of the perspiration effluent 310D from the textile film 322D. The textile film 322D in the fourth state includes minimal, reduced, or no amount of liquid, having evaporated substantially all of the perspiration effluent 310C and resulting a minimal amount of or absence of perspiration effluent 310D. The textile film 322D can be at a lower temperature than the biological object 330D or a temperature corresponding to the biological object 330D, and can have a temperature higher than an ambient environment surrounding the textile apparatus 320B increasing or maximized in response to receiving substrate heat 334C received from the biological object 330D. The textile film 322D can complete internal evaporation of the perspiration effluent 310D by contact with the substrate 324B and the substrate heat 334C received therefrom. The substrate 324B can be at a lower temperature than the biological object 330D or a temperature corresponding to the biological object 330D, and can have a temperature higher than an ambient environment surrounding the textile apparatus 320B increasing or maximized in response to receiving substrate heat 334C received from the biological object 330C. The perspiration duct 332D in the second state can cease emitting perspiration in response to sufficient heat transfer away from the biological surface 330D and transmission of the substrate heat 334C to the textile apparatus 320B.

The biological object 330D in the fourth state can be in a state of substantially fully releasing the perspiration effluent 310D, and continuing to further emit heat. The perspiration effluent 310D in the fourth state can be substantially fully evaporated from the textile film 322D in response to heating by the substrate heat 334C received from the substrate 324B.

Evaporation time with in accordance with the textile apparatus 320A-D can be advantageously significantly shorter than with conventional textiles. Skin temperature in accordance with the textile apparatus 320A-D can also be advantageously significantly lower than conventional textiles during evaporation, demonstrating that the human body can evaporate sweat faster with even lower skin temperature when wearing an example textile in accordance with present implementations. Furthermore, present implementations exhibit a linear relationship between average evaporation rate and average skin temperature d with a certain amount of liquid, biofluid, or the like. As one example, an example textile in accordance with present implementations can demonstrate a higher evaporation rate than cotton with the same initial liquid amount and same skin temperature.

Figure 4:
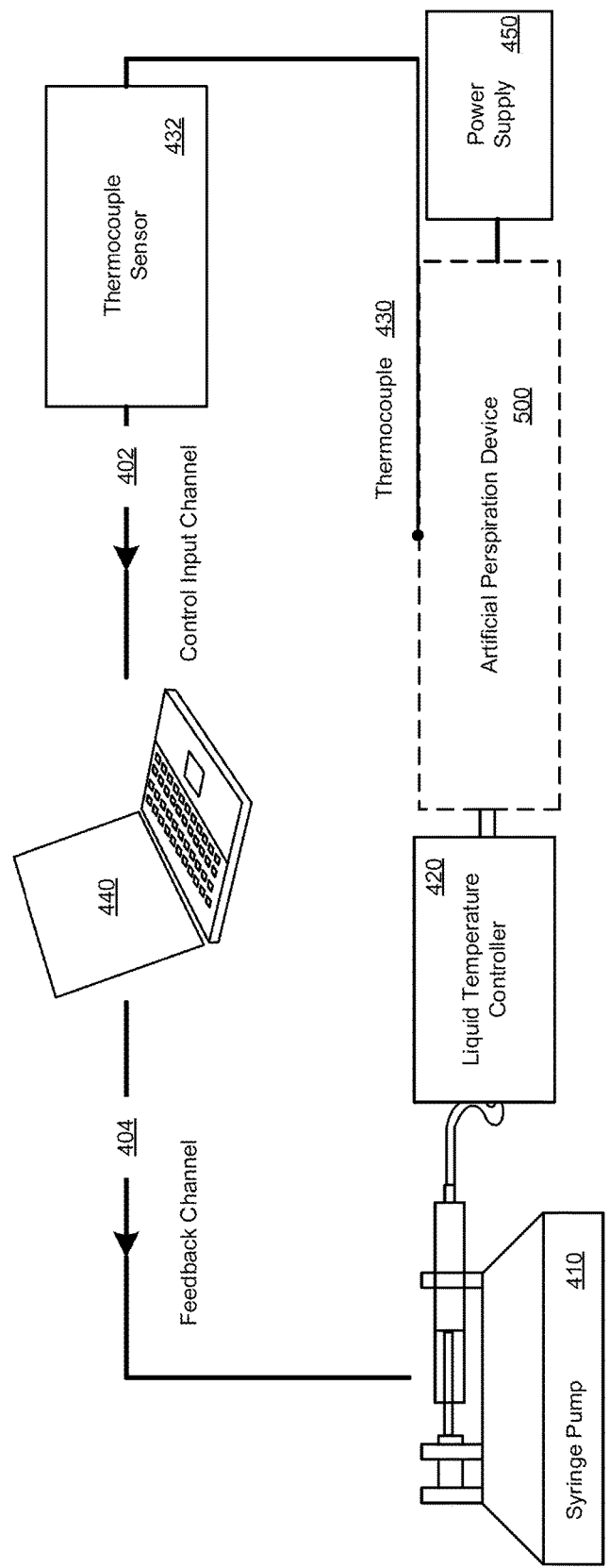
FIG. 4 illustrates an example artificial perspiration system, in accordance with present implementations.

FIG. 4 illustrates an example artificial perspiration system, in accordance with present implementations. As illustrated by way of example in FIG. 4, an example artificial perspiration system 400 includes a syringe pump 410, a liquid temperature controller 420, a thermocouple 430, a thermocouple sensor 432, a feedback control device 440, a power supply 450, and an artificial perspiration device 500.

The syringe pump 410 includes a plunger structure and is operable to expel liquid from the plunger structure. The liquid containable in and expellable by the syringe pump 410 can include water, biofluid, or the like, and can include liquid having one or more physical characteristics corresponding to biofluid. As one example, biofluid can be human sweat. The syringe pump 410 can include a motor, solenoid, or the like operable to move one or more components of the plunger to mechanically, electromechanically, or the like, expel water from the syringe pump 410. A tube, pipe, or the like can be connectably attached to an outlet of the syringe pump to transport the liquid expelled therefrom. The rate of expulsion of water from the syringe pump 410 can be controlled by actuation of the motor, solenoid, or the like by wired, wireless, or like control. The syringe pump can expel water at a constant or variable rate in response to actuation of the motor, solenoid, or the like. The liquid temperature controller 420 is operable to heat water received by the syringe pump 410, and can include at least one liquid tube, liquid channel, liquid reservoir, or the like. The liquid temperature controller 420 is operable to maintain liquid received from the syringe pump 410 at a substantially constant temperature. As one example, the substantially constant temperature can be 37° C., any temperature corresponding to temperature of biofluid, or the like. The liquid temperature controller can be operatively coupled at an inlet thereof to a tube, pipe, or the like coupled or couplable to the syringe pump 410.

The thermocouple 430 includes at least a pair of electrical terminals operatively coupled to the artificial perspiration device 500. The thermocouple can be operatively coupled to a surface of the artificial perspiration device corresponding to an artificial sweating skin structure. A temperature detected at the thermocouple 430 can vary in response to variation in temperature of liquid expelled at the artificial perspiration device 500 after being received from the liquid temperature controller 420.

The thermocouple sensor 432 includes one or more electrical components, electronic components, or the like operable to determine a temperature of the artificial sweating skin structure of the artificial perspiration device 500. The thermocouple sensor 432 can generate a digital, analog, or like electrical response corresponding to a particular temperature at the artificial sweating skin structure. The thermocouple sensor 432 can monitor temperature at the artificial sweating skin structure in real time and can transmit temperature data to the computer in real time.

The feedback control device 440 includes at least one computing device operable to detect a temperature detected at the thermocouple sensor 432 and generate a corrected temperature command for operating the syringe pump 410. As one example, the feedback control device 440 can instantly alternate the pumping rate of syringe pump that corresponds to the sweating rate of artificial sweating skin in response to a temperature change detected at the artificial sweating skin structure of the artificial perspiration device 500. The thermocouple sensor 432, syringe pump 410 and power supply 450 can all be controlled by a program which can alter pumping rate according to the thermometer reading in real time. Thus, a rate of liquid expelled at the artificial sweating skin structure can be responsive to the temperature at the artificial sweating skin structure, to mimic the feedback control loop for the human body's temperature and sweating feedback control mechanism. The feedback control device can include a control input channel 402 and a feedback channel 404.

The control input channel 402 is operable to communicatively couple the thermocouple sensor 432 to the feedback control device 440. In some implementations, the control input channel 402 is operable to communicate one or more instructions, signals, conditions, states, or the like between one or more of the thermocouple sensor 432 and the feedback control device 440. In some implementations, the control input channel 402 includes one or more digital, analog, or like communication channels, lines, traces, or the like. As one example, the control input channel 402 is or includes at least one serial or parallel communication line among multiple communication lines of a communication interface. The feedback channel 404 is operable to communicatively couple the feedback control device 440 to the syringe pump 410. In some implementations, the feedback channel 404 is operable to communicate one or more instructions, signals, conditions, states, or the like between one or more of the feedback control device 440 and the syringe pump 410. In some implementations, the feedback channel 404 includes one or more digital, analog, or like communication channels, lines, traces, or the like. As one example, the feedback channel 404 is or includes at least one serial or parallel communication line among multiple communication lines of a communication interface.

The power supply 450 includes one or more electrical, electronic, electromechanical, electrochemical, or like devices or systems for at least one of receiving, storing and distributing input power. In some implementations, the power supply 450 includes one or more stacks of batteries. In some implementations, the power supply 450 includes lithium-ion or like energy storage. In some implementations, the power supply 450 includes a plurality of battery units variously or entirely integrated with, integrable with, or separable from the system 400.

The artificial perspiration device 500 includes an artificial sweating skin structure that can generate sweat uniformly from one or more fabricated artificial perspiration outlets therein. The artificial perspiration device 500 can be filled with water in advance of operation. A perspiration skin temperature associated with the artificial perspiration device 500 can be set to a particular temperature. As one example, the perspiration threshold skin temperature can be set to 34.5° C., over which the sweating rate was linearly dependent on skin temperature. As another example, if no ambient relative humidity is specified, the ambient relative humidity can be 40%±5%.

Figure 5:
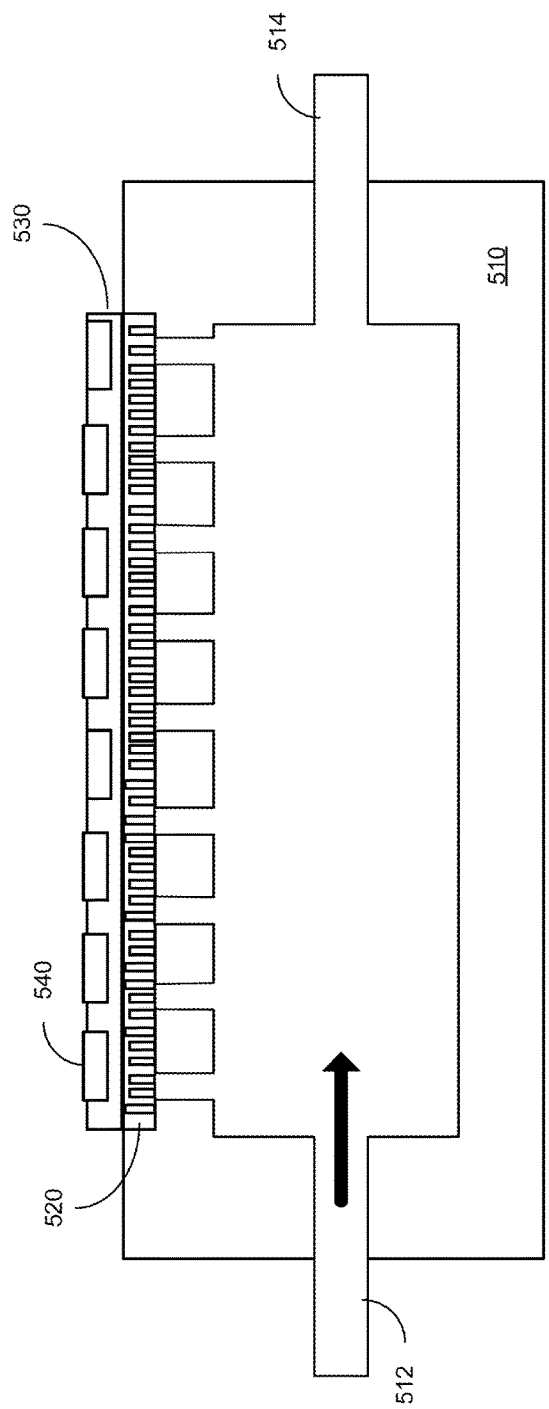
FIG. 5 illustrates an example artificial perspiration device further to the example artificial perspiration system of FIG. 4.

FIG. 5 illustrates an example artificial perspiration device further to the example artificial perspiration system of FIG. 4. As illustrated by way of example in FIG. 5, an example artificial perspiration device 500 includes a liquid reservoir 510, a perforated heater layer 520, a wicking layer 530, and a hydrophobic layer 540 including one or more liquid transmission openings 542.

The liquid reservoir 510 includes a cavity operable to store, hold, or the like, liquid received from one or more of the syringe pump 410 and the liquid temperature controller 420. The liquid reservoir 510 can include a liquid chamber 502, a flow inlet 512, and a flow outlet 514.

The liquid chamber 502 is a cavity in the liquid reservoir operable to expel liquid through one or more outlets. As one example, the liquid chamber 502 can be an enclosed cuboid cavity. As another example, water in the liquid chamber 502 can be forced out upwards through channels on an upper boundary thereof. The flow inlet 512 includes at least one opening operably coupled to at least one of the syringe pump 410 and the liquid temperature controller 420. The flow outlet 514 includes at least one opening separate and distinct from the flow inlet 512. The flow outlet 514 can be operably coupled to at least one of the syringe pump 410 and the liquid temperature controller 420 to recycle liquid expelled through the flow outlet 514. The flow outlet 514 can also be a wastewater outlet not including any feedback to one or more of the syringe pump 410 and the liquid temperature controller 420.

The perforated heater layer 520 includes a perforated hydrophilic heater. The perforated heater layer 520 can generate heat and can concurrently allow liquid to pass therethrough from a lower boundary of the perforated heater layer 520 coupled to the liquid chamber 502, to an upper boundary of the perforated heater layer 520 opposite to the lower boundary of the perforated heater layer 520.

The wicking layer 530 includes one or more openings allowing water to pass therethrough from a lower boundary thereof to an upper boundary thereof. The wicking layer 530 can be a Janus-type wicking layer with limited water outlets, and can be disposed contactably on an upper surface of the perforated heater layer. Thus, the wicking layer 530 can simulate the surface of human skin and can generate substantially uniform artificial perspiration from each artificial sweat pore corresponding to the one or more openings therein.

The hydrophobic layer 540 is contactably disposed on the wicking layer 530 and includes one or more portions inhibiting the flow of liquid therethough. As one example, water can diffuse into the unmodified bottom portion of the wicking layer 530 with strong wicking ability and be transported to the top surface, while the hydrophobic baffles on the top surface can confine water outflow to the unmodified hydrophilic locations. The baffles of the hydrophobic layer 540 can be constructed by placing a mask on the wicking layer 530, and spraying diluted polydimethylsiloxane (PDMS) solution on the masked wicking layer 530. Subsequently, the mask can be removed and the wicking layer 530 can be subjected to a process of drying and curing. Thus, the uncovered top surface of the wicking layer can be modified to be hydrophobic. The liquid transmission openings 542 correspond to the unmodified hydrophilic locations. Accordingly, water wicked from the bottom can flow out only from the limited water outlets uniformly to mimic human body perspiration. As one example, evaporative resistance at the hydrophobic layer 540 can be calculated by $$R_{ef} = \frac{(P_s - P_a) \cdot A}{H} - R_{ebp},$$

where $P_s$ is the water vapor pressure at the surface wicking layer 530. As one example, the saturation at the temperature of the surface, $P_a$ can correspond to the water vapor pressure in the air, where A is the area of the plate test section, His the power input, and $R_{ebp}$ is the value measured without any textile samples.

Figure 6:
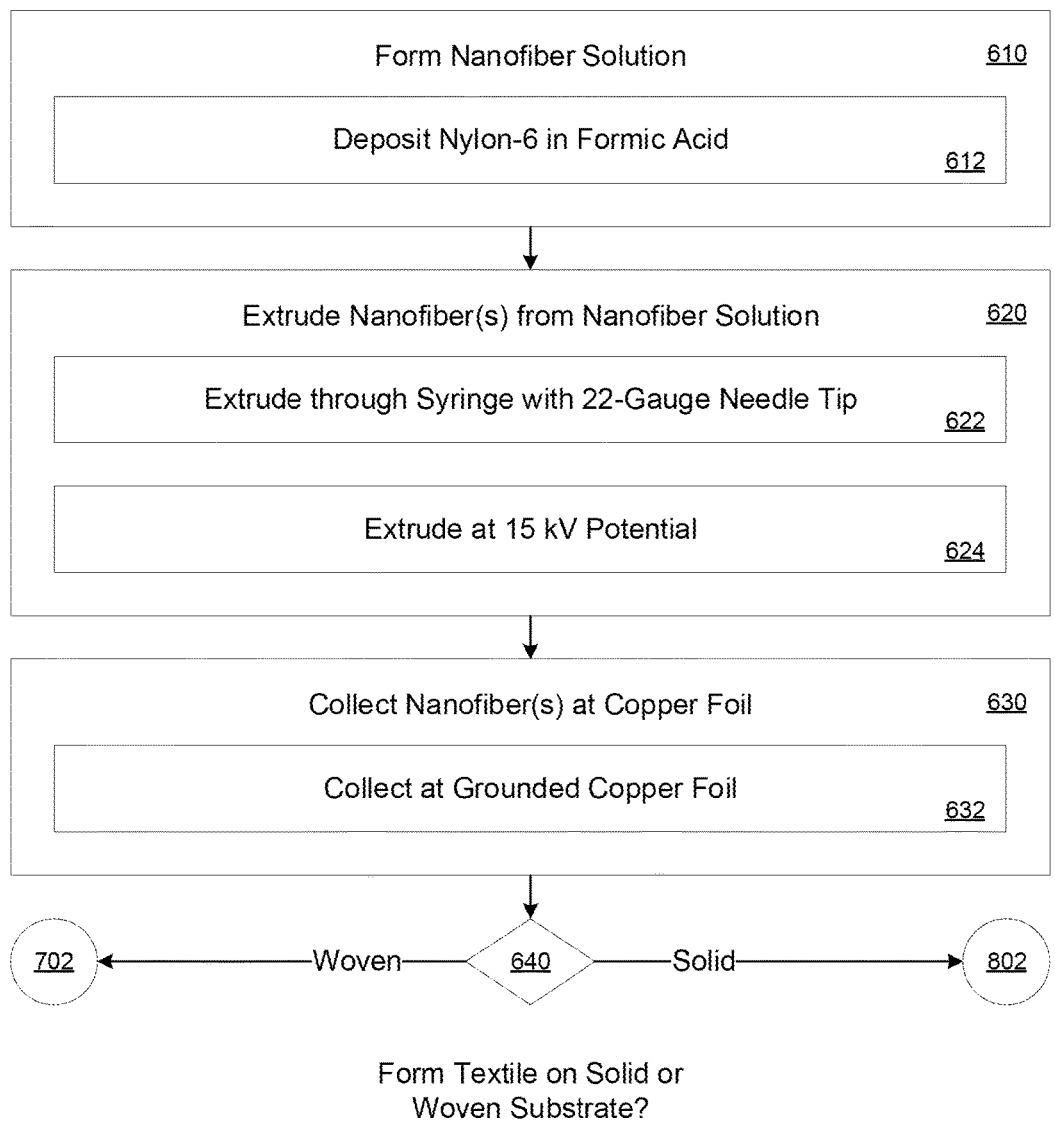
FIG. 6 illustrates an example method of manufacturing a heat conducting and biofluid transporting textile, in accordance with present implementations.

FIG. 6 illustrates an example method of manufacturing a heat conducting and biofluid transporting textile, in accordance with present implementations. In some implementations, at least one of the example devices 100 and 200 is manufactured by method 600 according to present implementations. In some implementations, the method 600 begins at step 610.

At step 610, the example system forms a nanofiber solution. In some implementations, step 610 includes step 612. At step 612, the example system deposits nylon-6 in formic acid. The method 600 then continues to step 620.

At step 620, the example system extrudes one or more nanofibers from the nanofiber solution. In some implementations, step 620 includes at least one of steps 622 and 624. At step 622, the example system extrudes the nanofibers through a syringe. The syringe can have a 22-gauge needle tip or the like. At step 624, the example system extrudes the nanofibers at a predetermined voltage potential. The predetermined voltage potential can be 15 kV. The method 600 then continues to step 630.

At step 630, the example system collects the nanofibers at a collection surface. The collection surface can be a copper foil. It is to be understood that that the collection surface can be a conductive surface, a metallic surface, or the like, not limited to copper. In some implementations, step 630 includes step 632. At step 632, the example system collects the nanofibers at a grounded collection surface. As discussed above, the collection surface can be copper. The method 600 then continues to step 640.

At step 640, the example system determines whether to form a textile on a woven substrate or a substrate sheet. In accordance with a determination to form the textile on a woven substrate, the method 600 continues to step 702. Alternatively, in accordance with a determination to form the textile on a substrate sheet, the method 600 continues to step 802.

Figure 7:
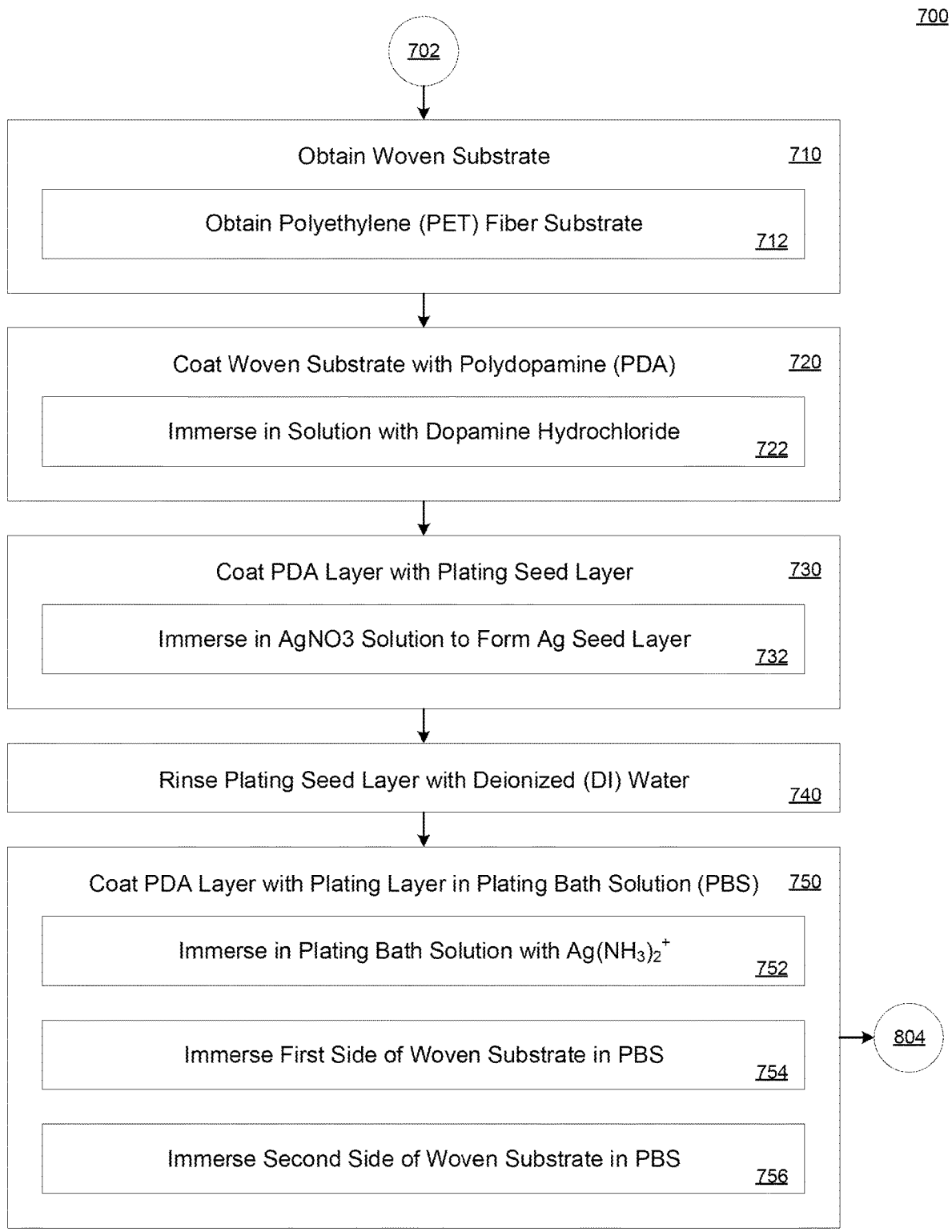
FIG. 7 illustrates an example method of manufacturing a heat conducting and biofluid transporting textile, further to the example method of FIG. 6.

FIG. 7 illustrates an example method of manufacturing a heat conducting and biofluid transporting textile, further to the example method of FIG. 6. In some implementations, at least one of the example devices 100 and 200 is manufactured by method 700 according to present implementations. In some implementations, the method 700 begins at step 702. The method 700 then continues to step 710.

At step 710, the example system obtains a woven substrate. In some implementations, step 710 includes step 712. At step 712, the example system obtains a woven substrate including one or more polyethylene (PET) fibers. The polyethylene fibers can be woven together into a textile sheet, cloth, fabric, or the like. PET can advantageously avoid strong water wicking by itself, and allow perspiration to travel through to an opposite surface from the skin by a nanofiber film. The method 700 then continues to step 720.

At step 720, the example system coats the woven substrate with polydopamine (PDA). In some implementations, step 720 includes step 722. At step 722, the example system immerses the woven substrate at least partially in a solution including dopamine hydrochloride (dopamine HCl). The method 700 then continues to step 730.

At step 730, the example system at least partially coats the PDA layer with a plating seed layer. In some implementations, step 730 includes step 732. At step 732, the example system immerses the woven substrate having the PDA coating at least partially in a silver nitrate ($AgNO_3$) solution. The method 700 then continues to step 740.

At step 740, the example system rinses the woven substrate having the plating seed layer with deionized water. The method 700 then continues to step 750.

At step 750, the example system coats the plating seed layer of the woven substrate with a plating layer. The plating seed layer can improve the bonding affinity of the plating layer to the woven substrate as compared with a plating layer coating step not including the plating seed layer. In some implementations, step 750 includes at least one of steps 752, 754 and 756. At step 752, the example system immerses the woven substrate having the plating seed layer at least partially in a solution including $Ag(NH_3)_2^+$. At step 754, the example system immerses a first side of the woven substrate in the plating bath solution. The first side can correspond to a first planar surface of the textile surface of the woven substrate. At step 756, the example system immerses a second side of the woven substrate in the plating bath solution. The second side can correspond to a second planar surface of the textile surface of the woven substrate opposite to the first planar surface previously immersed. Thus, the woven substrate can be fully coated by the plating layer on each side of the woven substrate independently. The method 700 then continues to step 804.

Figure 8:
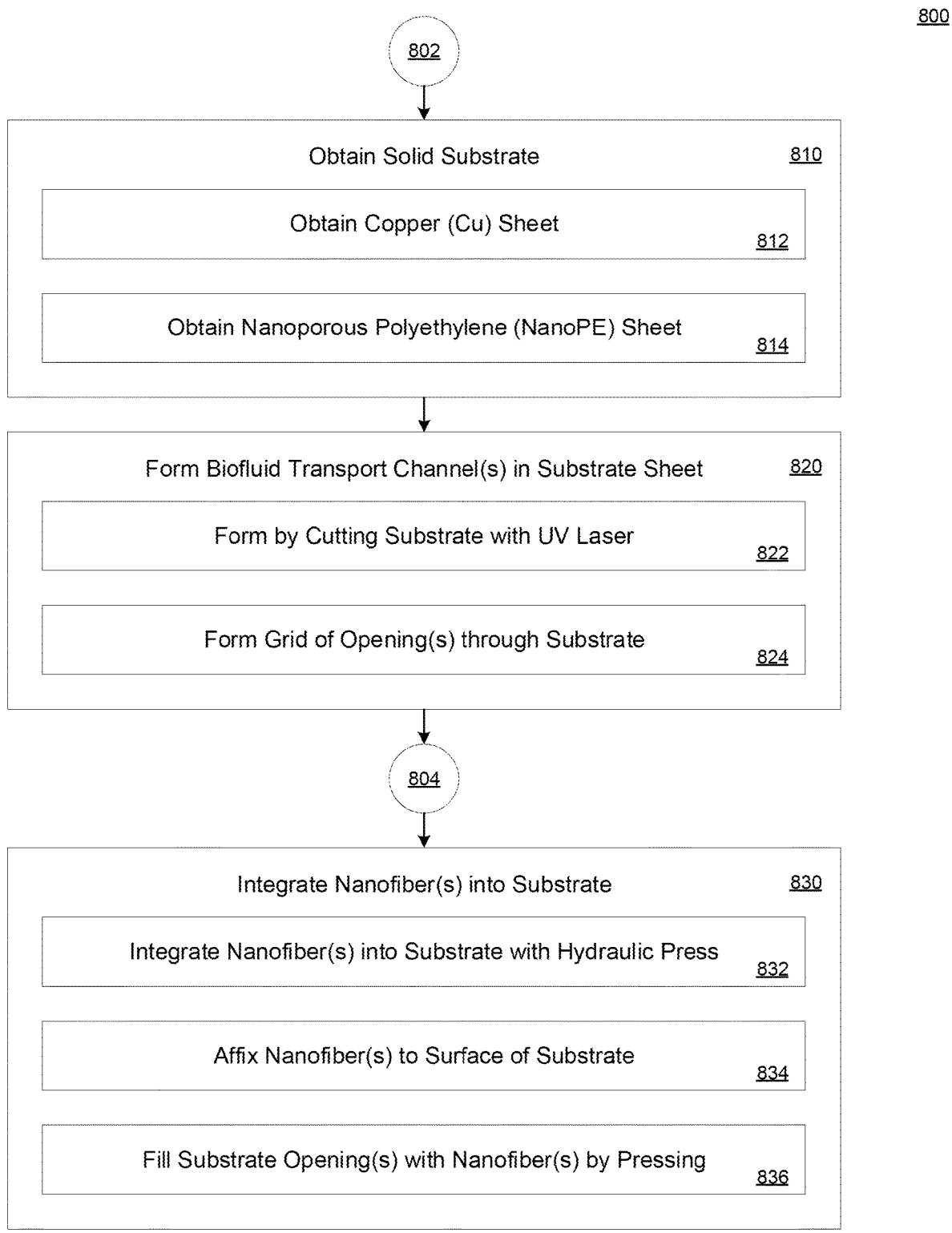
FIG. 8 illustrates an example method of manufacturing a heat conducting and biofluid transporting textile, further to the example method of FIG. 7.

FIG. 8 illustrates an example method of manufacturing a heat conducting and biofluid transporting textile, further to the example method of FIG. 7. In some implementations, at least one of the example devices 100 and 200 is manufactured by method 800 according to present implementations. In some implementations, the method 800 begins at step 802. The method 800 then continues to step 810.

At step 810, the example system obtains a substrate sheet. A substrate sheet can be a solid sheet of metal, polymer or the like, or any combination thereof. In some implementations, step 810 includes at least one of steps 812 and 814. At step 812, the example system obtains a substrate sheet including copper. At step 814, the example system obtains a substrate sheet including a nanoporous polyethylene (nanoPE) sheet. The method 800 then continues to step 820.

At step 820, the example system forms one or more biofluid transport channels in the substrate sheet. The biofluid transport channels can be or include, holes, recesses, cavities, openings, or the like, in, through, or the like, the substrate sheet. In some implementations, step 820 includes at least one of steps 822 and 824. At step 822, the example system forms the biofluid transport channels by cutting the substrate sheet with an ultraviolet (UV) laser. At step 824, the example system forms a grid of holes, recesses, cavities, openings, or the like, in, through, or the like, the substrate sheet. The method 800 then continues to step 804. At step 804, the method 800 then continues to step 830.

At step 830, the example system integrates the one or more nanofibers into the substrate. The nanofibers can form a textile film that sits on the substrate and is compressed, pressed, or the like, into permanent contact with the substrate. In some implementations, step 830 includes at least one of steps 832, 834 and 836. At step 832, the example system integrate the nanofibers into the substrate by a hydraulic press. The substrate and nanofiber film can be placed in contact with each other at planar surfaces thereof. The combined substrate and nanofiber film can be then sandwiched between plates of a hydraulic press, for example, to integrate the two layers. At step 832, the example system affixes the nanofibers to a surface of the substrate. The surface of the substrate can include one or more of a planar face, surface, or the like, of the substrate. The surface of the substrate can also include one or more interior surfaces of the holes, recesses, cavities, openings, or the like, in, through, or the like, the substrate sheet or gaps between woven fibers of the woven substrate. At step 836, the example system at least partially fills one or more of the holes, recesses, cavities, openings, or the like, in, through, or the like, the substrate sheet or gaps between woven fibers of the woven substrate with the nanofibers by pressing. The press lamination process can generate nanofibers on the substrate sheet denser and with smaller space among the nanofibers than nanofibers disposed in the holes, openings, cavities, or the like, of the substrate sheet. The pressing can include, as discussed above, pressing by hydraulic press. Capillarity difference result from this morphology difference can advantageously benefit evaporation, because liquid transport to the nanofibers closest to the heat conductive substrate sheet of the example textile accelerates evaporation of liquid capture therein. In some implementations, the method 800 ends at step 830.

The herein described subject matter sometimes illustrates different components contained within, or connected with, different other components. It is to be understood that such depicted architectures are illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Further, unless otherwise noted, the use of the words "approximate," "about," "around," "substantially," etc., mean plus or minus ten percent.

The foregoing description of illustrative implementations has been presented for purposes of illustration and of description. It is not intended to be exhaustive or limiting with respect to the precise form disclosed, and modifications and variations are possible in light of the above teachings or may be acquired from practice of the disclosed implementations. It is intended that the scope of the invention be defined by the claims appended hereto and their equivalents.

What is claimed is:

1. A textile apparatus for transporting perspiration and heat, the textile apparatus comprising:
    a substantially planar and heat-conducting substrate including a plurality of channels each disposed through the substrate from a first substantially planar surface of the substrate to a second substantially planar surface of the substrate opposite to the first substantially planar surface of the substrate, the plurality of channels extending in a direction substantially perpendicular to and disposed between the first and second substantially planar surfaces of the substrate and defining holes through the substrate; and
    a textile film including one or more fibers disposed on the first substantially planar surface of the substrate and at least partially within each of the plurality of channels and extending to the second substantially planar surface.

2. The textile apparatus of claim 1, wherein the substrate comprises a copper sheet.

3. The textile apparatus of claim 1, wherein the substrate comprises a nanoporous polyethylene sheet.

4. The textile apparatus of claim 1, wherein the substrate comprises a textile including one or more woven polyethylene fibers.

5. The textile apparatus of claim 1, wherein the one or more fibers comprise a plurality of fibers collected and located proximate to each other.

6. The textile apparatus of claim 5, wherein the plurality of fibers are formed together in a woven configuration.

7. The textile apparatus of claim 1, wherein the one or more fibers comprise nanofibers with water absorbing properties.

8. The textile apparatus of claim 7, wherein the nanofibers include nylon 6.

9. The textile apparatus of claim 7, wherein the nanofibers have a diameter less than 5 µm.

10. The textile apparatus of claim 7, wherein the nanofibers are arranged in a substantially integrated structure and integrally disposed on the first substantially planar surface of the substrate.

11. The textile apparatus of claim 10, wherein the second substantially planar surface of the heat-conducting substrate includes nanofibers exposed through the channels.

* * * * *